United States Patent [19]

Lipton

[11] Patent Number: 5,770,441

[45] Date of Patent: Jun. 23, 1998

[54] METHODS, APPARATUSES AND KITS FOR THE GROWTH AND/OR IDENTIFICATION OF MICROORGANISMS

[76] Inventor: Stewart Lipton, 712 Clearview Dr., Glenview, Ill. 60025

[21] Appl. No.: 723,916

[22] Filed: Sep. 30, 1996

[51] Int. Cl.$^6$ .................................................. C12M 3/00
[52] U.S. Cl. ................................. 435/289.1; 435/305.1; 435/305.2; 435/305.3; 435/305.4; 435/307.1; 435/810
[58] Field of Search .............................. 435/29, 30, 31, 435/32, 34, 39, 243, 254.1, 256.8, 287.9, 288.3, 288.4, 288.7, 289.1, 305.1, 305.2, 305.3, 305.4, 307.1, 810

[56] References Cited

U.S. PATENT DOCUMENTS

| | | | |
|---|---|---|---|
| Re. 35,286 | 6/1996 | Nelson et al. | 435/243 |
| 2,736,656 | 2/1956 | Marshall | 99/171 |
| 2,858,224 | 4/1958 | Darrah | 99/161 |
| 3,078,986 | 2/1963 | Ushkow | 206/56 |
| 3,497,320 | 2/1970 | Blackburn et al. | 23/230 |
| 3,582,285 | 6/1971 | Hamilton | 23/259 |
| 3,736,042 | 5/1973 | Markovits et al. | 350/95 |
| 3,787,290 | 1/1974 | Kaye | 435/288.4 |
| 3,881,993 | 5/1975 | Freake et al. | 435/287.7 |
| 4,011,350 | 3/1977 | Markovits et al. | 427/2.13 |
| 4,263,256 | 4/1981 | Morle | 422/66 |
| 4,387,972 | 6/1983 | Valencia et al. | 350/95 |
| 4,396,579 | 8/1983 | Schroeder et al. | 422/52 |
| 4,767,702 | 8/1988 | Cohenford | 435/24 |
| 4,867,308 | 9/1989 | Crawford et al. | 206/330 |
| 5,167,924 | 12/1992 | Clark | 422/58 |
| 5,417,576 | 5/1995 | Hill | 435/299 |

OTHER PUBLICATIONS

Nunc Product Brochure, "SonicSeal Slide Wells", Nunc, Inc. Naperville, IL.

Hill, "Thin Agar Film for Enhanced Fungal Growth and Microscope Viewing in a New Sealable Fungal Culture Case," *J. of Clinical Microbiology*, vol. 34, No. 9, pp. 2140–2142 (Sep. 1996).

*Primary Examiner*—David A. Redding
*Attorney, Agent, or Firm*—Fitch, Even, Tabin & Flannery

[57] ABSTRACT

The present invention provides slide system apparatuses, kits and methods for the growth and/or identification of microorganisms, such as fungi. The slide system apparatuses comprise a unitary member containing one or more compartments in which microorganisms may grow, one or more solid support matrices present in each of these compartments, dehydrated media, which may be hydrated with water, present within, or on one or more surfaces of, each of the solid support matrices, a cover sheet lying over the open end of each compartment and secured to the upper surfaces of the unitary member which surround the open end of each compartment, and an optional adhesive layer present on the lower surface of each cover sheet and/or present on the upper surfaces of the unitary member which surround the open end of each compartment.

21 Claims, 2 Drawing Sheets

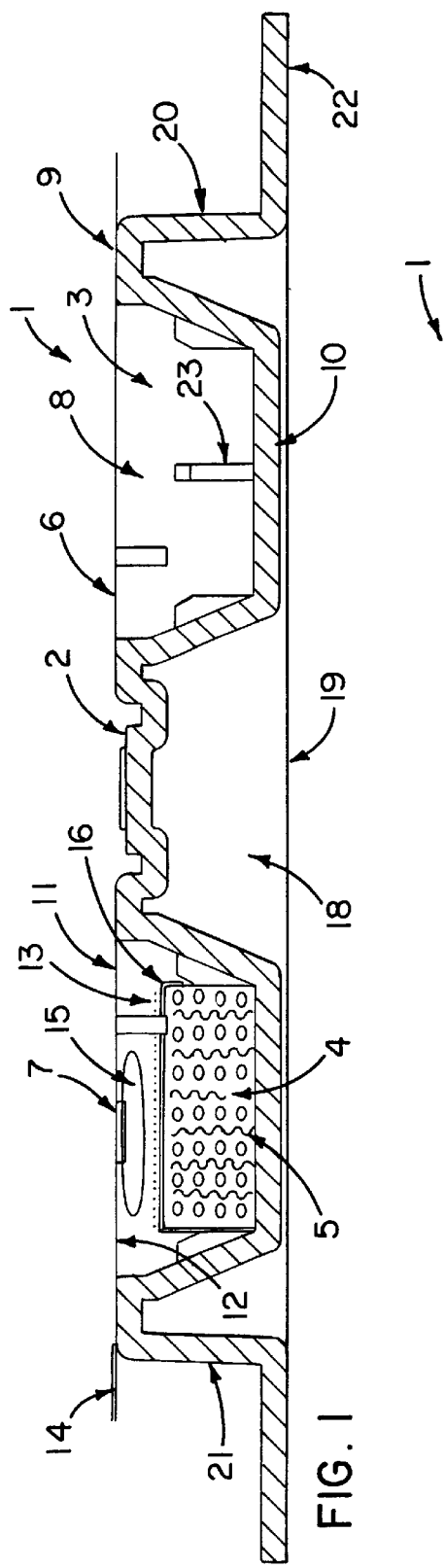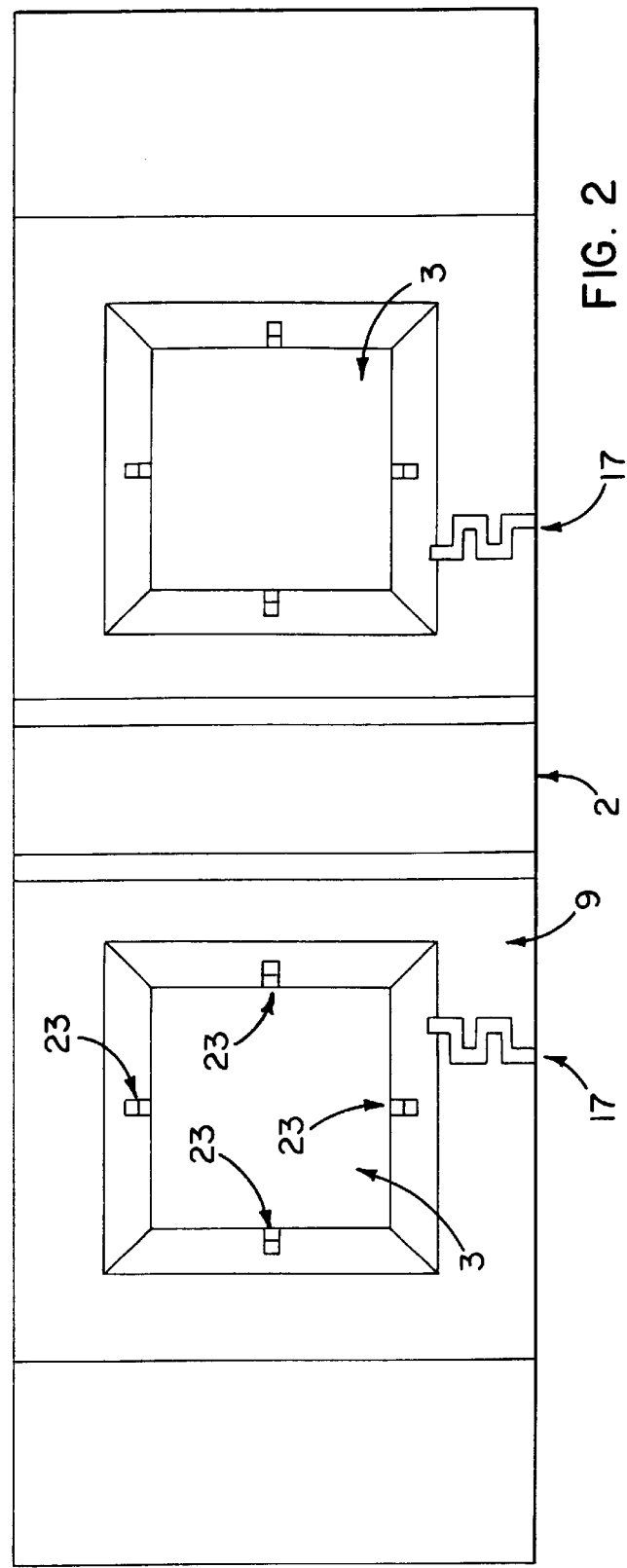

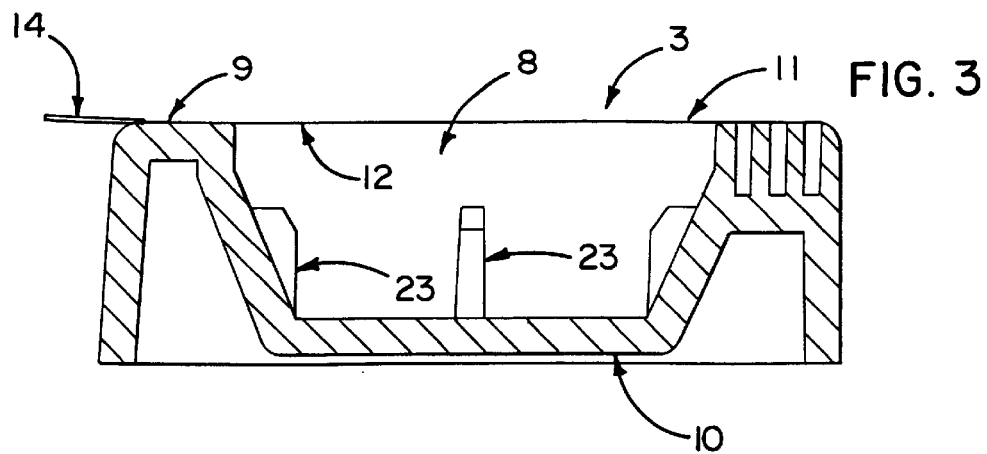
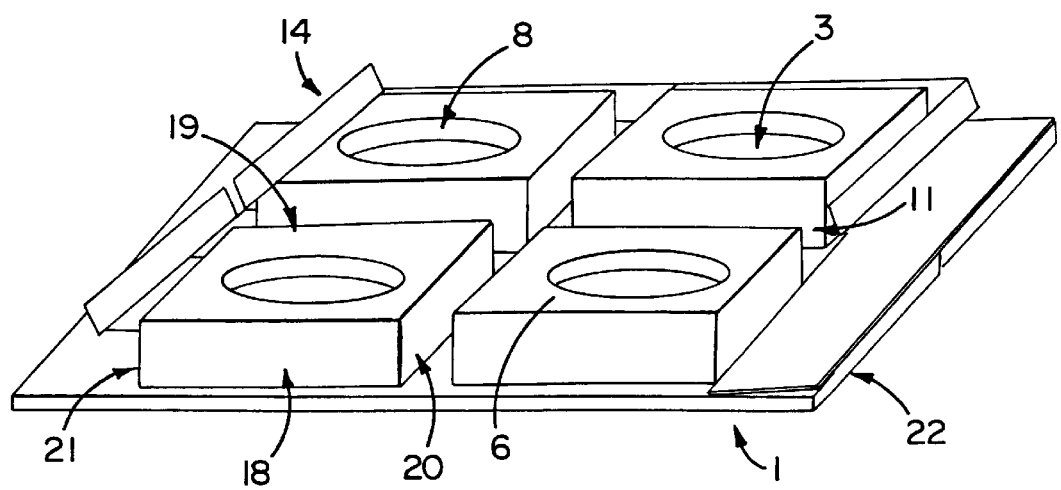
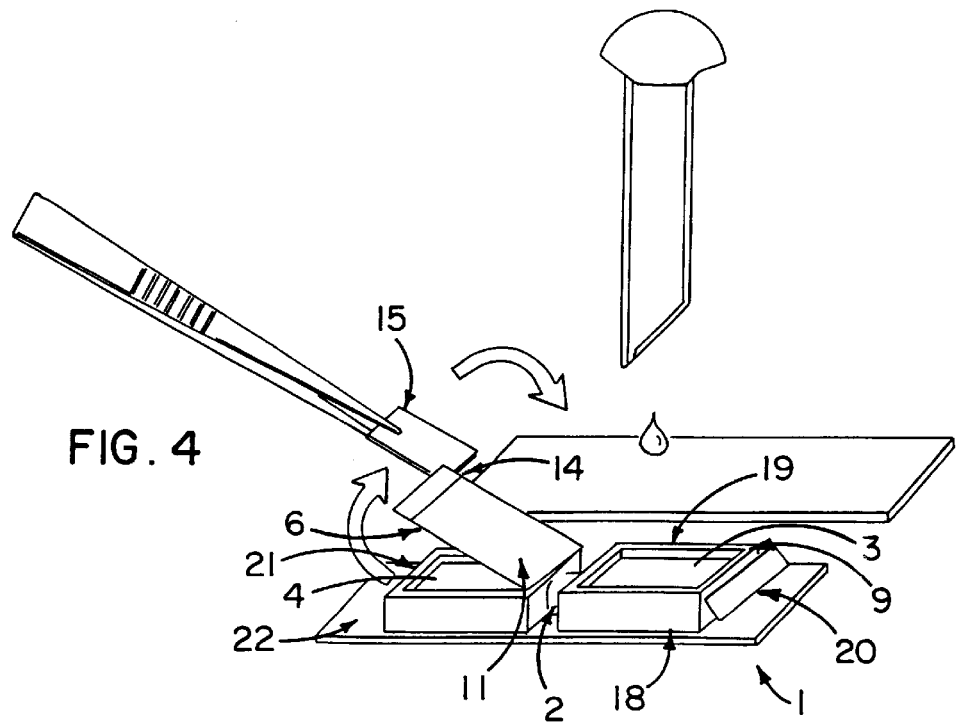

METHODS, APPARATUSES AND KITS FOR THE GROWTH AND/OR IDENTIFICATION OF MICROORGANISMS

BACKGROUND OF THE INVENTION

1. Field of the Invention

The present invention generally relates to the art of culturing diagnosing microorganisms, and more particularly pertains to a slide system apparatus for the growth and/or identification of microorganisms, such as fungi, a kit for the growth and/or identification of microorganisms, such as fungi, and a process for growing and identifying microorganisms, such as fungi.

2. Background and Description of Related Art a. Background

As an initial, somewhat crude test to determine whether or not fungi are present or absent in a sample, a physician will often take a skin scraping or sample of hair suspected of containing fungi from a patient, and digest the skin or hair on a glass slide with a caustic agent, such as potassium hydroxide. The caustic agent will dissolve the skin or hair, such that other items present in the sample may be viewed under a microscope. If fungi are present in the sample, then the physician will see structures under the microscope which are characteristic of fungi (filamentous forms). This will permit a determination that fungi are present in the sample, but will not permit the proper identification of the fungi.

For the proper identification of the fungi, a culture will often subsequently be made of the fungi by growing the fungi, which generally employs glass petri dishes, which are costly to purchase, clean and maintain. Once the fungi have grown to a stage which is sufficient to permit their proper identification, a slide culture is generally made from this initial culture. The slide culture generally consists of a square of agar medium which has been inoculated with a sample of the culture of the fungi initially made, and which has been placed upon a microscope slide with a cover glass on top of the culture which is present on the slide. The slide culture is then generally incubated in a humid environment. After such incubation, identification of the fungi is generally accomplished by removing the cover glass from the slide, placing the cover glass on another microscope slide on top of a drop of lacto-phenol cotton blue stain and viewing the fungi under a microscope.

The laboratory diagnosis (proper identification) of fungi is often difficult and time-consuming.

Generally, it is best to examine a fungus microscopically when the culture first begins to grow and forms conidia or spores, and again a few days later. In many instances, the manner of conidiation or sporulation, which is very important to the correct identification of the fungi, is obscured in old cultures.

Further, many fungi are polymorphic and, therefore, observation of the fruiting bodies as they grow is essential. Such observation is not possible with currently-existing methods for growing cultures of fungi.

The accurate identification of filamentous moulds and other cultures of fungi is based upon the microscopic examination of the sporulating parts of a colony. Currently-employed methods for such identification include: (1) tease mount methods; (2) cellophane tape mounts; and (3) slide cultures. Each of these methods has disadvantages.

While tease preparations (preparations of a fungal colony removed from an agar surface made by teasing apart the mycelial mass of the colony on a glass slide with two dissecting needles) may be employed, these preparations have several disadvantages. First, microscope slide preparations must be prepared from cultures of fungi. Second, if too much growth is removed when making such a microscope slide preparation, if the growth is not teased apart well, or if the material is taken from a non-sporulating area of growth, it may be difficult to discern sporulating structures. Third, spores are often disrupted during preparation of the microscope slide. Thus, this method does not always preserve the original position and structure of the conidia, spores and the like.

Cellophane tape mount methods for studying the microscopic morphology of a fungal culture, which involve the placement of a piece of clean cellophane tape on the surface of a fungal colony and subsequently on a glass slide, also has the drawback of requiring that the organism to be identified first be grown on plated medium, and subsequently be identified on a microscope slide preparation.

Slide cultures are often employed for the identification of conidial fungi, since it is necessary to observe the natural configuration of the conidia on the conidiogenous cell. The slide culture system consists of a mini-incubation chamber designed to produce optimum conditions for sporulation.

In order to prevent the contamination of the fungi cultures, each of the methods described above must be performed under a laminate flow hood, which is both inconvenient and expensive.

Similar disadvantages exist with currently-employed methods for growing and identifying other types of microorganisms.

The slide systems apparatuses of the present invention, which have been named the MYCO-EASE™ systems, and the methods and kits of the present invention, solve the above-described problems by permitting the growth of a culture of microorganisms, such as fungi, in a closed system which permits the microorganisms to be viewed at any time under a microscope through the slide system apparatus itself without interrupting the growth of the microorganisms, without virtually any risk that the culture will become contaminated, and without ever having to prepare or use any microscope slides. This, in turn, permits the individual who is working with the culture to view the growing fungi (or other microorganisms) on a daily basis without disturbing the growing fungi in any manner until the fungi have grown to a stage where they can be properly identified (until they have formed the reproduction bodies known as conidia, which will permit their proper identification and diagnosis). At this time, the user can properly identify and diagnose the fungi without the use of a microscope slide by simply placing the slide system apparatus on a microscope, and viewing the growing fungi through the slide system apparatus. These methods, apparatuses and kits allow a culture of fungi (or other microorganisms) to be grown and subsequently viewed under a microscope in a simpler and more cost-effective manner, with fewer steps, and in a more rapid manner, than with currently-existing methods for growing cultures of fungi (or other microorganisms), and for viewing these cultures under a microscope. These methods, apparatuses and kits also eliminate the requirement for glass petri dishes, which are costly to purchase, clean and maintain, and which cannot be used for viewing growing microorganisms without having to make a microscope slide preparation of the growing microorganisms. The petri dish does not fit properly on a microscope, and it becomes foggy after time.

b. Description of the Related Art

Current methods for culturing and identifying various types of fungi are described in A. Balows et al., *Manual of*

*Clinical Microbiology* (ASM Press, 5th Edition, Washington, D.C., 1995) and D. Larone, *Medically Important Fungi, A Guide to Identification* (ASM Press, 3rd Edition, Washington, D.C., 1995).

Walge Nunc International (Naperville, Ill.) commercially markets a detachable plastic, four-well media chamber which is sonically welded to a slide. This product combines a miniature culture vessel with a tissue culture treated slide.

U.S. Pat. No. 2,736,656 discloses individual food packages made by forming an elongated strip of thermoplastic material into a series of cups, each cup being sealed with a strip of thermoplastic material.

U.S. Pat. No. 2,858,224 discloses a method for processing eggs which includes the use of a plastic container which receives the eggs, and is then sealed.

U.S. Pat. No. 3,078,986 discloses a container formed from plastic material which includes a flexible cover sheet which has an adhesive coating.

U.S. Pat. No. 3,497,320 discloses a chemical analyzer having a plurality of disposable reaction chambers.

U.S. Pat. No. 3,582,285 discloses a disposable test package which includes a plurality of compartments which are overlaid with a material which prevents the premature dispensing of prepackaged reagents.

U.S. Pat. No. 3,736,042 and U.S. Pat. No. 4,011,350 disclose a microscope slide assembly and a method of preparing this assembly.

U.S. Pat. No. 4,263,256 discloses cuvettes formed as a continuous integral strip.

U.S. Pat. No. 4,387,972 discloses a transparent microscope slide for the diagnostic analysis of liquid specimens.

U.S. Pat. No. 4,396,579 discloses a luminescence detection device. FIG. 5 of this patent shows a base with a plurality of wells which can be covered with a membrane.

U.S. Pat. No. 4,767,702 discloses a filter paper assay test strip for the identification of Neisseria species.

U.S. Pat. No. 4,867,308 discloses a tape for storage and retrieval of electronic components.

U.S. Pat. No. 5,167,924 discloses a flow-through apparatus which includes a well covered with a membrane.

U.S. Pat. No. 5,417,576 discloses a device for both growing and observing microbiological organisms under a microscope without removing the organisms from the container.

Unlike the slide system apparatus of the present invention, which contains dehydrated media present within a solid support matrix, the device disclosed in the '576 patent does not contain a solid support matrix, and contains an agar film. Column 9, Lines 19–25, of the '576 patent teaches away from the use of media which is dried by stating the following:

"The thinness of the agar film provides for advantages such as mentioned above. Care must be taken not to expose the film to air too much so as to prevent the film from drying. The case as according to the present invention allow sealing of the chamber to deter drying of the film."

The use of a non-dehydrated media, such as agar, significantly limits storage stability and shelf life. A significant advantage which results from the use of a media which is dehydrated is the ability to store an apparatus containing such media for long periods of time. Slide system apparatuses within the present invention have been successfully stored without any deleterious effects for periods of at least about one year, with storage periods of longer than one year being possible, depending on the type of media.

Other components of slide system apparatuses within the present invention which are not disclosed by the '576 patent include: (1) a cover sheet which may be repeatedly removed from, and readhered to, the slide system apparatus; (2) protrusions present in compartments contained in the slide system apparatuses which hold solid support matrices in place; and (3) an opening containing one or more curves or right angles through which air can flow from the outside environment into each of the compartments which are present in the slide system apparatuses, with no microbiological filter being necessary.

Further, an in contrast to the devices disclosed in the '576 patent, the slide system apparatuses of the present invention may contain more than one compartment, with each compartment containing the same or different dehydrated media, and containing the same or different microorganism. This permits the growth and identification of multiple different types of microorganisms in one apparatus at the same time and the placement of a variety of medias in one apparatus.

U.S. Pat. No. 5,427,779 discloses a method of modifying a solid polymer.

Each of the documents described hereinabove discloses methods and apparatuses which are different from the methods, apparatuses and kits of the present invention. Thus, the methods, apparatuses and kits of the present invention are distinct from that which has been described in the art.

All patents and publications referred to throughout the specification are hereby incorporated herein by reference, without admission that such is prior art.

SUMMARY OF THE INVENTION

The present invention provides a slide system apparatus for the growth and/or identification of microorganisms, such as fungi, comprising:

(1) a unitary member containing one or more compartments in which microorganisms may grow, and containing one or more openings through which air may flow from the outside environment into each of the compartments;

(2) one or more solid support matrices present in each of the compartments contained in the unitary member;

(3) dehydrated media present within, or on one or more surfaces of, each of the solid support matrices;

(4) a cover sheet lying over the open end of each compartment and secured to the upper surfaces of the unitary member which surround the open end of each compartment, and having a pull tab;

(5) an optional adhesive layer present on the lower surface of each cover sheet and/or present on the upper surfaces of the unitary member which surround the open end of each compartment; and (6) an optional cover glass.

The present invention also provides a kit for the growth and/or identification of microorganisms comprising:

(1) a slide system apparatus comprising:
  (a) a unitary member containing one or more compartments in which microorganisms may grow, and containing one or more openings through which air may flow from the outside environment into each of the compartments;
  (b) one or more solid support matrices present in each of the compartments contained in the unitary member;
  (c) dehydrated media present within, or on one or more surfaces of, each of the solid support matrices;

(d) a cover sheet lying over the open end of each compartment and secured to the upper surfaces of the unitary member which surround the open end of each compartment, and having a pull tab;

(e) an optional adhesive layer present on the lower surface of each cover sheet and/or present on the upper surfaces of the unitary member which surround the open end of each compartment;

(f) an optional cover glass; and (2) one or more:

(a) hydrating liquids;

(b) cover glasses;

(c) tools for inoculating the solid support matrices with a sample containing fungi;

(d) tools for grasping other items present within the kit;

(e) microscope slides;

(f) reagents for staining fungi samples; and/or (g) reagents for making permanent microscope slide stain preparations.

The present invention further provides a method for growing and/or identifying microorganisms in a sample containing microorganisms employing the above-described slide system apparatuses or kits comprising:

(1) grasping the pull tab present on the cover sheet and peeling the cover sheet across a portion of a compartment to allow some or all of the dehydrated media to be exposed;

(2) placing a hydrating liquid into the compartment;

(3) allowing the media to become partially or fully dissolved;

(4) inoculating the media with a sample containing microorganisms;

(5) placing a cover glass upon the solid support matrix;

(6) placing the cover sheet back onto one or more of the upper surfaces of the unitary member; and (7) incubating the slide system apparatus under conditions which are sufficient to allow microorganisms present within the sample to grow to a state which permits their proper identification.

BRIEF DESCRIPTION OF THE DRAWINGS

FIG. 1 is a front view of a preferred embodiment of the slide system apparatuses of the present invention which contains 2 square compartments.

FIG. 2 is a top view of a preferred embodiment of the slide system apparatuses of the present invention which contains 2 square compartments.

FIG. 3 is an end view of a preferred embodiment of the slide system apparatuses of the present invention which contains 2 square compartments.

FIG. 4 shows the production of a permanent stain preparation with the use of the slide system apparatuses of the present invention.

FIG. 5 is a front view of another embodiment of the slide system apparatuses of the present invention, which contains 4 round compartments.

DETAILED DESCRIPTION OF THE INVENTION

1. Definitions

For purposes of clarity, the terms and phrases used throughout this specification and in the appended claims are defined in the manner set forth directly below.

The term "culture" as used herein means the propagation of microorganisms in special media conductive to their growth.

The term "dermatophyte" as used herein means a fungus which is parasitic upon the skin, and embraces the imperfect fungi of the genera Microsporum, Epidermophyton and Trichophyton. This type of fungus is also called cutaneous fungus or dermatomyces.

The terms "fungus" and "fungi" as used herein means any of a group of eukaryotic protists, including, but not limited to, mushrooms, yeasts, rusts, molds, smuts, dermatophytes, etc., which are generally characterized by the absence of chlorophyll, and by the presence of a rigid cell wall composed of chitin, mannans and, sometimes, cellulose. They are usually of simple morphological form or show some reversible cellular specialization, such as the formation of pseudoparenchymatous tissue in the fruiting body of a mushroom. The names of certain fungi are described hereinbelow under the heading "*Types of Fungi.*"

The terms "medium" and "media" as used herein mean any substance, either solid or liquid, or a combination thereof, which may be employed for the cultivation, isolation, mounting, identification and/or storage of microorganisms, such as fungi. Examples of such media include sabaraudus dextrose broth, pablum cereal agar, potato dextrose agar, potato flakes agar, cornmeal agar, v-8 juice agar, blood, chocolate agar, egg white and/or yolks, polyvinyl alcohol, acetate ascospore agar, Gorodkowa medium, carbon assimilation medium, nitrate assimilation medium, basal medium, brain heart infusion agar, casein agar, cornmeal agar, dermatophyte test medium, Loeffler medium, Lysozyme medium, starch hydrolysis agar, Trichophyton agar, tyrosine agar and xanthine agar. These substances may be unsupplemented or supplemented with any of a variety of vitamins, antibiotics, minerals and/or amino acids. Many of these media are described in M. McGinnis, *Laboratory Handbook of Medical Mycology* (Academic Press, Inc., New York, 1980) and A. Balows et al., *Manual of Clinical Microbiology*, supra., each of which is incorporated herein by reference.

2. Description of Invention a. General Information

In one aspect, the present invention provides a slide system apparatus for the growth and/or identification of microorganisms comprising:

(1) a unitary member containing one or more compartments in which microorganisms may grow, and containing one or more openings through which air may flow from the outside environment into each of the compartments;

(2) one or more solid support matrices present in each of the compartments contained in the unitary member;

(3) dehydrated media present within, or on one or more surfaces of, each of the solid support matrices;

(4) a cover sheet lying over the open end of each compartment (that end of the compartment which is exposed to the outside environment) and secured to the upper surfaces of the unitary member which surround the open end of each compartment, and having a pull tab;

(5) an optional adhesive layer present on the lower surface of each cover sheet (that surface of the cover sheet which faces the open end of the compartment) and/or present on the upper surfaces of the unitary member which surround the open end of each compartment; and (6) an optional cover glass.

In another aspect, the present invention provides a kit for the growth and/or identification of microorganisms comprising:

(1) a slide system apparatus comprising:
   (a) a unitary member containing one or more compartments in which microorganisms may grow, and containing one or more openings through which air may flow from the outside environment into each of the compartments;
   (b) one or more solid support matrices present in each of the compartments contained in the unitary member;
   (c) dehydrated media present within, or on one or more surfaces of, each of the solid support matrices;
   (d) a cover sheet lying over the open end of each compartment (that end of the compartment which is exposed to the outside environment) and secured to the upper surfaces of the unitary member which surround the open end of each compartment, and having a pull tab;
   (e) an optional adhesive layer present on the lower surface of each cover sheet (that surface of the cover sheet which faces the open end of the compartment) and/or present on the upper surfaces of the unitary member which surround the open end of each compartment;
   (f) an optional cover glass; and
(2) one or more:
   (a) hydrating liquids;
   (b) cover glasses;
   (c) tools for inoculating the solid support matrices with a sample containing fungi;
   (d) tools for grasping other items present within the kit;
   (e) microscope slides;
   (f) reagents for staining fungi samples; and/or
   (g) reagents for making permanent microscope slide stain preparations.

In yet another aspect, the present invention provides a method for growing and/or identifying microorganisms in a sample containing fungi employing the above-described slide system apparatuses or kits comprising:

(1) grasping the pull tab present on the cover sheet and peeling the cover sheet across a portion of a compartment to allow some or all of the dehydrated media to be exposed;
(2) placing a hydrating liquid into the compartment;
(3) allowing the media to become partially or fully dissolved;
(4) inoculating the media with the sample containing microorganisms;
(5) placing a cover glass upon the solid support matrix;
(6) placing the cover sheet back onto one or more of the upper surfaces of the unitary member; and
(7) incubating the slide system apparatus for a time period, and at a temperature, sufficient to allow microorganisms present within the sample to grow to a state in which they can be identified.

The most preferred embodiment of the present invention is a slide apparatus for growing and identifying fungi which: (1) is made from polystyrene; (2) has two compartments in a square shape, and about 17 mm×17 mm in width and about 8 mm in height; (3) is about 25.4 mm in width, about 76.5 mm in length and about 8 mm in height (so that it fits conveniently on a standard microscope); (4) has a solid support matrix which is made from cellulose acetate, which is the shape of a doughnut and which is about 11.5 mm, with a hole which is about 6 mm wide; (5) employs sabaraudus dextrose broth as the dehydrated media; and (6) which has a cover glass which is larger in size than the solid support matrix, and which is round in shape.

The present invention relates to novel methods, slide system apparatuses and kits for the culturing and/or identification of microorganisms, such as any type of fungus. These slide system apparatuses are use-friendly, attractive, inexpensive and constructed in a manner which facilitates the mass production thereof.

The slide system apparatuses of the present invention may by of any convenient shape, such as square, rectangular, triangular, round, oval or in the shape of a hexagon or an octagon. However, a rectangular shape, as is shown in the figures presented hereinbelow, is preferred.

The slide system apparatuses of the present invention may by of any convenient size. The size of these systems will vary, depending upon the number of compartments, chambers or wells which are placed or formed therein. If the microorganisms growing in the slide system apparatuses of the invention will be viewed under a microscope, the slide system apparatuses should be of a size which fits within a conventional light microscope (of a size which fits under the objective lens of the microscope, and which may be held by conventional calipers of microscopes). Preferably, the slide system apparatuses of the present invention will be of a size ranging from about 5 mm×5 mm to about 500 mm×500 mm in length and/or width and from about 2 mm to about 100 mm in height, preferably from about 25 mm 25 mm to about 100 mm×100 mm in length and/or width and from about 4 mm to about 15 mm in height, with about 25.4 mm in width, about 76.5 mm in length and about 8 mm in height being most preferred.

The slide system apparatuses of the present invention may contain any desired number of compartments, chambers or wells, but preferably contain from about 1 to about 100 compartments, and more preferably contain from about 2 to about 50 compartments, with about 2 to about 4 compartments being most preferred.

Specific methods, slide system apparatuses and kits within the scope of the invention include, but are not limited to, the methods, slide system apparatuses and kits discussed in detail herein and/or illustrated in the drawings contained herein.

Contemplated equivalents of the methods, slide system apparatuses and kits described herein and/or illustrated in the drawings contained herein include methods, slide system apparatuses and kits which otherwise correspond thereto, and which have the same general properties and/or components thereof, wherein one or more simple or other variations of steps or components is made.

For the purpose of illustrating the slide system apparatuses of the present invention, there are shown in the drawings, which form a material part of this disclosure, two different embodiments of the slide system apparatuses of the invention, which are the preferred embodiments of the slide system apparatuses of the invention.

The various components of the slide system apparatuses of the invention are generally arranged in the manner shown in the drawings. However, the present invention is not limited to the precise arrangements, configurations, dimensions and/or instrumentalities shown in these drawings. These arrangements, configurations, dimensions and instrumentalities may be otherwise, as circumstances require.

Different specific embodiments of the slide system apparatuses of the present invention will now be described with reference to the drawings.

The drawings contained herein are provided to enable one of ordinary skill in the art to practice the present invention. These drawings are merely illustrative, however, and should not be read as limiting the scope of the invention as it is claimed in the appended claims.

SLIDE SYSTEM APPARATUSES

Referring to the drawings, the slide system apparatuses 1 of the present invention for the growth and identification of fungi comprise:

(1) a unitary member 2 containing one or more compartments 3 in which the growth of microorganisms may take place, and containing one or more openings 17 through which air may flow from the outside environment into each of the compartments 3;

(2) one or more solid support matrices 4 present in each of the compartments 3 which is present, or formed, in the unitary member 2;

(3) dehydrated media 5, which may be hydrated with water or another appropriate hydrating liquid, present within, or on one or more surfaces of, each of the solid support matrices 4;

(4) a cover sheet 6 lying over the open end 8 of each compartment 3 (that end of the compartment 3 which is exposed to the outside environment) and secured to the upper surfaces of the unitary member 9 which surround the open end 8 of each compartment, and having a pull tab 14; and (5) an optional adhesive layer 7 present on the lower surface of each cover sheet 12 (that surface of the cover sheet which faces the open end of the compartment 8) and/or present on the upper surfaces of the unitary member 9 which surround the open end 8 of each compartment.

UNITARY MEMBER

The purpose of the unitary member 2 is that of forming the compartments 3 in which dehydrated media 5 may be placed, and in which fungi 13 may be cultured.

The unitary member 2 has an upper surface 9 to which one or more cover sheets 6 may be adhered and a lower surface 10.

The unitary member 2 is preferably a rectangular continuous blister sheet of a flexible, transparent film or plastic which cannot easily be ruptured by tearing or other means. Such a unitary member 2 may be, for example, a vinyl thermoplastic film of about 0.003 mm thick.

The unitary member 2 is made in a manner known by those of skill in the art, such as by extrusion, blown or tenter processes.

The unitary member 2 may be of any convenient size and thickness, and generally ranges in a size of from about 5 mm×5 mm to about 500 mm×500 mm, and preferably ranges in size from about 25 mm×25 mm to about 100 mm×100 mm, with about 25.4 mm in width and about 63.5 mm in length being most preferred. The unitary member generally ranges in thickness from about 0.001 mm to about 0.75 mm, and preferably ranges in thickness from about 0.002 mm to about 0.005 mm, with about 0.003 mm being most preferred. The size of the unitary member will depend upon the number of compartments (or chambers or wells) which the user desires to have placed or formed therein.

The unitary member 2 may be of any convenient shape, such as square, rectangular, triangular, round, oval, or in the shape of a hexagon or an octagon. However, the square and rectangular shapes are preferred because these shapes more easily allow compartments to be formed therein.

Any material which has the characteristics of clarity and rigidity, such as styrene, are preferably employed for use in the unitary member 2. Such materials are known by those of skill in the art, and are available from commercially-available sources known by those of skill in the art. Such materials include, but are not limited to, a variety of polymers and copolymers, such as polyvinyl chloride, nylon, polyethylene terephthalate, polyethylene, polypropylene, polystyrene and similar materials. It is more preferable that the unitary member be formed from a material which is clear (so that the growing microorganisms may be clearly viewed and identified), hydrophobic in nature, resistant to aqueous and/or organic solvents, such as alcohol, being employed by the user, nonflexble (rigid to some extent), breathable, can be gas sterilized, can be injection molded, can have light waves pass therethrough and can retain humidity in a virtually closed environment. Some of these features are desirable for the microorganisms, such as fungi, which may grow in a compartment 3 formed from this material, because many microorganisms are phototrophic (like light), and because microorganisms such as fungi generally need air, humidity and an ambient temperature in order to properly grow. Typically, the unitary member 2 will be made from a sheet of clear, preformed polyvinyl chloride or polystyrene having compartments 3 and, optionally, protrusions 23, injection molded therein for receiving solid support matrices 4 and dehydrated media 5, and for growing fungi 13. Polystyrene is preferably employed.

The unitary member 2 will contain, or have formed therein, one or more compartments 3 (or chambers or wells) having appropriate spaces for receiving solid support matrices 4 and dehydrated media 5, and having an appropriate environment in which various types of microorganisms 13 may properly grow.

From one to a plurality (such as two, four, ten, twenty, thirty, forty, fifty, etc.) of compartments 3 may be injection molded into the unitary member 2 by conventional injection molding methods known by those of skill in the art. The compartments 3 are generally rigid chambers injection molded into the unitary member 2, and which project downwards from the lower surface 10 of the unitary member (that surface which is not attached to the cover sheets 6). Where more than one of these compartments or chambers 3 is present in the unitary member 2, they are preferably spaced apart at regular intervals ranging from about 0.001 mm to about 100 mm, preferably ranging from about 0.01 mm to about 10 mm, most preferably ranging from about 0.2 mm to about 2 mm, with about 0.29 mm being most preferred, but may also be irregularly spaced. Each of the one or more compartments 3 which may be formed into the unitary member 2 may be of any convenient size, and generally ranges in a size of from about 1 mm×1 mm to about 500 mm×500 mm in length or width and from bout 2 mm to about 100 mm in height, and preferably ranges in size from about 5 mm×5 mm to about 20 mm×20 mm in length or width and from about 3 mm to about 15 mm in height, with about 17 mm×17 mm in width and about 8 mm in height being most preferred.

Each of these compartments 3 may be of any convenient shape, such as the shape of a square, a rectangle, a triangle, a hexagon, an octagon, or the compartments may be round or oval in shape. However, the square and rectangle shapes are preferred because these shapes of the compartments 3 are more easily viewed and managed when present on a microscope.

It is preferable, but not critical, to have each of the compartments 3 formed into the unitary member 2 to be of about the same size and shape, and to be similarly spaced apart.

Because the compartments 3 are generally formed into the unitary member 2, the compartments 3 will generally be made of the same material from which the unitary member 2 is made. Although it is preferable to form the compartments 3 from the unitary member 2, it is possible to make the slide system apparatuses 1 of the present invention by adhering one or more separatelyformed compartments 3 together in a manner known by those of skill in the art with an adhesive which may be employed to accomplish this purpose, such as with various types of glue or other adhesive, or with various types of tape. It is not critical that the compartments 3 in which the fungi are to be grown are formed from a unitary piece of starting material.

Each compartment 3 present in a slide system apparatus of the invention 1 will also contain, or have formed therein, one or more relatively small openings 17 through which air can flow from the outside environment into each of the compartments 3. Because fungi generally are aerobic and, thus, need air in order to grow, these openings 17 supply air to the fungi (or other microorganisms) which are growing in an otherwise closed environment.

The size of the openings 17 should be large enough to allow air to enter a compartment 3 covered with a cover sheet 6 from the outside environment, and small enough so that contaminants from the outside environment do not enter the compartment 3 through the openings 17, and so that the microorganisms do not exit the slide system apparatus 1 through these openings 17. The size of the opening 17 will generally range from about 0.25 mm to about 1.5 mm, and will preferably range from about 0.5 mm to about 1.0 mm.

The openings 17 may be of any convenient shape, such as a round hole, a square hole, a rectangular hole, a hole which contains several curves or right or other angles, for example, in a connected series, etc. FIG. 2 shows an apparatus of the invention 1 which has an opening 17 which looks like a maze (six right angles connected together), and which is preferred because its more elaborate shape provides several potential barriers to contaminants which may be present in the outside environment. In such an opening 17, no microbiological filters are necessary to prevent microbiological organisms from either entering or leaving the compartments 3.

In order to provide further support to the slide system apparatuses of the invention 1, the unitary member 2 may, optionally, also have one or more of the following formed therein by, for example, injection molding: (a) a front side 18; (b) a back side 19; (c) a right side 20; (d) a left side 21; and/or (e) one or more extensions 22 from any of the above-described sides of the unitary member 2. The unitary member 2 may, alternatively, have any other type of a base formed therein, or attached thereto, of any convenient shape and size which provides further support for the slide system apparatus 1 of the invention.

In order to hold a solid support matrix 4 in place in a compartment 3, a compartment 3 may, optionally, contain any of a number (1, 2, 3, 4, 5, 6, 7, 8, 9, 10, etc.) of protrusions 23 which face the solid support matrix 4. The protrusion 23 may be of any convenient size and shape, and may be present on any or all of the walls which form the compartment 3. Preferably, the protrusions are in the shape of a rectangle, and are from about 0.001 mm to about 5 mm in width, from about 0.1 mm to about 20 mm in height and from about 0.001 to about 10 mm in depth, and are more preferably from about 0.1 mm to about 1 mm in width, from about 1 mm to about 5 mm in height and from about 0.01 to about 5 mm in depth, with about 0.75 mm in width, about 2 mm in length and about 1.0 mm in depth being most preferred. When the compartment 3 is in the shape of a square or rectangle, there is preferably one protrusion from each of the four walls of the compartment 3, starting at the base of the compartment, as is shown in FIG. 1.

Although it is preferable to have the unitary member 2 formed from a material which is transparent, so that the user may view fungi or other microorganisms which are growing in the compartments 3 present in the unitary member 2, it is possible to form the unitary member 2 from an opaque or amber material, so as to prevent light from reaching microorganisms which may suffer from deleterious effects when exposed to light.

SOLID SUPPORT MATRICES

The purpose of the solid support matrix 4 is that of providing a support system (structure) on which the fungi 13 or other microorganisms may grow, and for storing and supplying media for microbial growth.

The solid support matrix (or matrices) 4 present in each compartment 3 present in the unitary member 2 may be of any convenient size, and generally ranges in a size of from about 8 mm in diameter and about 2 mm in height to about 20 mm in diameter and about 20 mm in height, and preferably ranges in size from about 10 mm in diameter and about 2 mm in height to about 15 mm in diameter and about 5 mm in height, with about 12 mm in diameter and about 5 mm in height being most preferred. The solid support matrix 4 will generally be of a size which is compatible with the size of the compartment 3 in which it is placed.

The solid support matrix 4 which is present in each compartment 3 may be of any convenient shape, such as the shape of a square, a rectangle, a triangle, a ball, a circle, a hexagon, an octagon, or in the shape of a doughnut (round in shape, with a round piece of the material removed from its center). However, the doughnut form is preferred because this shape allows the maximum amount of light to surround the growing fungi or other microorganisms, which results in the enhanced ability to view the microorganisms. Additionally, this shape of the matrix 4 will permit the observation of the growing microorganisms by the viewer both at the center of the matrix 4, and around the outer edges of the matrix 4, rather than just around the outer edges of the matrix. It is preferable, but not critical, to have the shape of the solid support matrix 4 be the same as the shape of the compartment 3 in which it is to be placed. The size and shape of the different solid support matrices 4 which may be present in a slide system apparatus of the present invention 1 need not be the same.

Any material upon which microorganisms, such as fungi, may grow, such as polyesters, may be employed for use as a solid support matrix 4. Such materials are generally spongy in nature (have the characteristics of a sponge), have pores, and include, but are not limited to cellulosic materials such as cellulose acetate, porous plastic and extruded plastic materials, and bonded fibers. The preferred solid support matrix 4 for use in the present invention is a bonded polyester (cellulose acetate) material known as TRANSORB® (American Filtrona Company, Richmond, Va.) which has the shape of a doughnut (the center removed from the material), and which is about 2.51 mm thick and is about 11.5 mm in diameter, with about a 6-mm hole removed from the center of the material.

DEHYDRATED MEDIA

The purpose of the dehydrated media 5, which may be hydrated with water or with another appropriate liquid known by those of skill in the art, which is present within each of the compartments 3 is that of allowing the microorganisms under examination to be cultivated, isolated, mounted, identified and/or stored.

The dehydrated media 5 is placed into the compartments 3 in liquid form. It is allowed to adsorb into the solid support matrix 4, and then it is dried by low heat in a manner known by those of skill in the art. For example, it may be dried for about two minutes in an oven preheated to about 90° C.

The amount of media which may be placed into each compartment will generally range from about 0.005 mL to about 1.0 mL, and will preferably range from about 0.02 mL to about 0.05 mL, with about 0.025 mL being most preferred. It is not necessary that each compartment which is present in a slide system apparatus 1 of the invention have the same type, or amount, of dehydrated media 5 placed therein.

Dehydrated media 5 which may be employed in the slide system apparatuses 1 of the invention include, but are not limited to, the various types of commercially-available media described hereinabove (sources of media include but are not limited to Beckton Dickinson, Cockeysville, Md.; Difco, Detroit, Mich.; Remel, Lenexa, Kans.; Gibco BRL, Gaithersburg, Md.; and Oxoid, Columbia, Md.)

COVER SHEETS

The purpose of the cover sheets 6 is that of keeping the compartments 3 which are present in the unitary member 2 free from moisture and free from contaminants which may be present in the outside environment.

Each cover sheet 6 has an upper surface 11, which is exposed to the outside environment, a lower surface 12, which faces the inside of a compartment 3. Each cover sheet 6 may have an optional layer of adhesive material present on its lower surface 12 in order to secure it to the upper surface 9 of the unitary member.

Each cover sheet will generally also have a pull tab 14, which may be pulled by the user, and which is generally formed by a portion of the cover sheet 6 extending beyond any of the upper surfaces 9 of the unitary member. It may or may not have adhesive present on its lower surface. The pull tab 14 may, alternatively, be formed by having one corner of the cover sheet 6 extending beyond any of the upper surfaces 9 of the unitary member, or by having one area or one corner of the cover sheet not be adhered to the upper surface of the unitary member 9. The form of the pull tab 14 is not critical. Any type of pull tab 14 which will allow the user to pull the cover sheet 6 in a desired direction will be suitable for use in the present invention.

It is preferable that the cover sheets 6 be both flexible and transparent, so that the cover sheets 6 may individually be conveniently peeled to some extent off from the open end 8 of a compartment 3, and so that one may view the fungi 13 or other microorganisms being cultivated in the compartment 3, respectively. However, the cover sheets 6 may also be made from materials which are not transparent, as is described above for the unitary member 2.

It is also preferable that the one cover sheet 6 be separately adhesively secured in some manner to the top of each compartment 3, so that each compartment 3 remains individually sealed and, therefore, free from moisture and contamination by the outside environment, until the Lime of hydration of the dehydrated media 5 which is present in the compartment 3. This also allows each compartment 3 which may be present in a slide system apparatus 1 of the present invention to be separately opened and used at the desired time of operation.

The cover sheets 6 may be of any convenient size, and generally range in size from about 1 mm×1 mm to about 300 mm×300 mm, and preferably range in size from about 5 mm×5 mm to about 100 mm×100 mm, with about 22 mm×65 mm being most preferred. The size of each cover sheet 6 may vary, depending upon whether the cover sheet is covering only one compartment 3 or is covering more than one compartment 3. It is preferable that one cover sheet 6 covers one compartment 3.

Each cover sheet 6 should be large enough to sufficiently cover the compartment 3 to which it will be attached in a manner which keeps the compartment 3 free from moisture and contaminants which may be present in the outside environment.

The cover sheets 6 may be of any convenient thickness, and generally range in thickness from about 0.001 mm to about 0.75 mm, and preferably range in thickness from about 0.01 mm to about 0.5 mm, with about 0.02 mm being most preferred. The thickness of the cover sheets 6 is not critical, and ordinarily will be maintained within a range which provides adequate protection of the contents present within the compartments 3, while still being capable of being peeled away from the upper surface of the unitary member 9 without rupture.

The cover sheets 6 may be of any convenient shape, such as square, rectangular, triangular, round, oval or of a hexagonal or octagonal shape, but should preferably be of the same shape as the compartments 3 to which they are attached, and are preferably square.

Any material which preferably is tough and tear-resistant may be employed for use as a cover sheet 6. A wide variety of commercially-available plastic or other materials may be employed for use as a cover sheet 6. Such materials include, but are not limited to, commercially-available polyethylene terephthalate, reinforced acetal resins, polyester, polyolefin, polyamide, polycarbonate and polysulfone films, combinations thereof. Any suitable adhesive may be employed to adhere a cover sheet 6 to the upper surfaces of the unitary member 9 which surround the open end 8 of the compartment which is to be covered. It is preferable that the lower surface of the cover sheet 12 be tacky in the areas of the cover sheet 6 which come into contact with the unitary member 2, such that the cover sheet may be repeatedly removed from, and readhered to, the upper surface of the unitary member 9.

ADHESIVE LAYER

The cover sheets 6 may be individually attached to the upper surfaces of the unitary member 9 which surround the open end 8 of the compartments over which they lie in any manner, and with any materials and equipment, known by those of skill in the art. For example, the cover sheets 6 may be so attached by heat-and/or pressure-sealing, by solvent welding, by gluing, with tape or otherwise.

The slide system apparatuses 1 of the present invention may contain an optional adhesive layer 7 present on the lower surface of the cover sheet 12 and/or on the upper surface of the unitary member 9 which may be employed to adhere one or more cover sheets 6 over one or more compartments 3 of the apparatuses 1. It is preferable that the cover sheets 6 have on their lower surface 12 a rubber-based adhesive which is tacky and, thus, which permits the cover sheets 6 to be repeatedly removed from, and adhered to, each of the upper surfaces of the unitary member 9.

Examples of materials which are suitable for use as the adhesive layer 7 are known by those of skill in the art, and include commercially available rubber, polyethylene, polyester, vinyl, acrylics or polyolefins, all of which are commercially available from sources known by those of skill in the art, and which may be applied by spraying, dripping, curtain rolling, roller coating or similar techniques known by those of skill in the art.

KITS

The kits of the present invention comprise one or more of the above-described slide system apparatuses 1 and one or more of the following additional pieces of equipment, each of which is known by those of skill in the art, and each of which is commercially available from sources known by those of skill in the art:

(1) one or more hydrating liquids, such as water present within a dropper bottle, or within a unit dose form;

(2) one or more means for inoculating one or more of the solid support matrices 4 with a sample which may contain fungi 13 or other microorganisms, such as a sterile inoculating swab or a disposable loop or needle;

(3) one or more means for grasping other items present within the kit, such as a pair of sterile, disposable, pointed forceps;

(4) one or more cover glasses;

(5) one or more microscope slides;

(6) one or more reagents or other means for staining fungi or other microorganism samples present on a microscope slide, or for making a permanent microscope slide stain preparation, such as a dropper bottle containing lactophenol cotton blue stain, lactol phenal basic fuchsin stain, or any of a variety of Myco-Perm™ stains or mounting fluids or which are available from Scientific Device Laboratory (Des Plaines, Ill.); and/or (7) other components or reagents which may be useful in making a microscope slide preparation of a fungi sample.

The purpose of the cover glasses 15 is to cover the growing fungi or other microorganisms in a prescribed area in order that the growing microorganisms 13 may be properly viewed through a microscope.

The cover glass 15 may, optionally, be a component of the slide system apparatus 1 of the invention. Alternatively, the cover glass 15 may not be a component of the slide system apparatus of the invention 1, but may be a component of a kit which contains the slide system apparatus 1 of the invention. In the former case, the cover glass 15 may, for example, be lightly adhered to the lower surface of the cover sheet 12 with, for instance, a drop of glue, so that it can easily be removed from the lower surface of the cover sheet 12 by the user at the time of its use.

The cover glasses 15 may be of any desired shape, such as round, square, triangular, rectangular, oval, or of a hexagonal or octagonal shape. A round cover glass is preferred because it appears to permit the clearest viewing of the growing fungi 13 or other microorganisms (because a maximal area is made for viewing the microorganisms).

The cover glasses 15 may be of any convenient size, and will generally range in size from about 1 mm×1 mm to about 300 mm×300 mm, preferably from about 5 mm×5 mm to about 50 mm×50 mm, with about 15 mm×15 mm being most preferred.

The cover glasses may be of any convenient thickness, and will most preferably be of a thickness of about 0.02 mm (or designated as No. 1), with a thickness ranging from about 0.001 mm to about 0.75 mm being preferred, and with a thickness ranging from about 0.01 mm to about 0.5 mm being more preferred.

The cover glasses 15 may be made of any glass or plastic material which will allow the purpose described above to be fulfilled.

STEPS OF METHOD

Fungi 13 or other microorganisms may be grown and identified with the use of the above-described apparatuses 1 and/or kits of the present invention in accordance with the general procedure described below, which is described with regard to the embodiment of the slide system apparatus of the invention 1 shown in FIG. 1. Although this general procedure is described with reference to one compartment 3, it is to be understood that this procedure may be employed separately with each of the compartments 3 which may be present in, or formed by, the unitary member 2.

(1) Peeling of Cover Sheet

By grasping, the pull tab 14 which is present on each cover sheet 6 which overlies, and which is secured over, the compartment 3 formed by the unitary member 2 is peeled by the user across a portion of the compartment 3 in any direction, in any manner, and to any extent (such as half of the way over the compartment 3) which allows the dehydrated media 5 present in the compartment 3 to be exposed, so that it may be hydrated with water or another hydrating liquid.

(2) Hydration of Media

Water or another appropriate hydrating liquid known by those of skill in the art, such as deionized water, phosphate buffer or another buffer having a pH which permits the growth of fungi 13 or other microorganisms, is then placed into the compartment 3 in a manner such that the dehydrated media 5 becomes hydrated (on the top of the solid support matrix 4, at the base of the solid support matrix 4, etc.). The liquid should be sterile, and the amount of liquid employed will generally range from about 0.005 ml to about 10 ml, and will preferably range from about 0.5 ml to about 5 ml, with about 0.3 ml being most preferred. It is preferable, but not critical, that the media become completely dissolved into the liquid before proceeding with this methodology. This is generally accomplished by waiting for a period of time generally ranging from about 1 minute to about 30 minutes, preferably ranging from about 2 minutes to about 5 minutes, after placing the liquid into the compartment 3 before performing the next step in the process. Some medias may dissolve instantaneously with addition of liquid.

(3) Inoculation of Sample

Once the dehydrated media 5 has become sufficiently dissolved (partially or completely) into the liquid, a sample of skin scraping from a patient, or a sample of other material suspected of containing, or known to contain, fungal growth, or a sample of fungi growing in some other media, is taken by twisting the inoculating swab (or other inoculating tool known by those of skill in the art for accomplishing this task, such as a loop or needle), over the sample, or by otherwise contacting the inoculating swab with the sample (patting, digging, etc.). If the sample is being taken from a fresh culture, it is preferable to remove the culture from the outside edge of the medium containing the culture. The inoculating swab or other tool is then contacted with the top of the solid support matrix 4, preferably with rubbing in a twisting motion, but in any manner known by those of skill in the art for inoculating media with a sample known to contain, or suspected of containing, fungi.

(4) Cover with Cover glasses

With a pair of forceps, or other similar tool known by those of skill in the art, which has preferably been sterilized, a cover glass 15, which is preferably round in shape, is then placed upon the upper surface 16 of the solid support matrix 4 (on that surface of the solid support matrix 4 which is exposed to the environment once the cover sheet 6 has been peeled off from a portion of the open end 8 of a compartment 3) in a manner such that the underneath surface of the cover glass 15 is in either partial or complete contact with the upper surface 16 of the solid support matrix 4. It is preferable that the entire underneath surface of the cover glass 15 be in complete contact with the upper surface 16 of the solid support matrix 4.

The condensation of water onto the cover glass 15 should be avoided because visualization of the growing fungi each day otherwise becomes difficult or even impossible. If condensation becomes a problem, the apparatus of the invention 1 should be incubated in an inverted position.

(5) Replacement of Cover Sheet

The cover sheet 6 should then be placed back onto one or more of the upper surfaces 9 of the unitary member 2, preferably in its original position, in order to keep contaminants from the outside environment away from the growing microorganisms, and to reduce condensation.

(6) Incubation

The entire slide system apparatus of the invention 1 is then incubated in any suitable apparatus for incubation, such as an incubator or chamber under conditions which are appropriate for the particular microorganisms being cultured to grow, as are known by those of skill in the art. This incubation will generally take place at a temperature generally ranging from about 23° C. to about 27° C., preferably ranging from about 24° C. to about 26° C., with about 25° C. being most preferred, for a period of time until the microorganisms are at the appropriate stage in their growth to be identified. Factors such as temperature, time, light conditions, duration of incubation and type of microorganisms being grown may need to be adjusted in a manner known by those of skill in the art for optimum growth. The incubation environment should generally also have humidity present.

(7) Viewing of Samples Under a Microscope

The growing cultures should be viewed under any appropriate microscope for such viewing, such as a light microscope, on a daily basis in order to monitor their growth and, with respect to fungi 13, the eventual production of conidia (the reproduction bodies which permit the proper identification and diagnosis of fungi). Conidia can form rapidly. No microscope slides are necessary for such viewing. The entire slide system apparatus 1 of the invention is placed on the microscope in the same area of the microscope that a microscope slide would normally be placed. The growing microorganisms are then viewed with the microscope through the slide system apparatus of the invention. Thus, the growing cultures are never disturbed, as they would be if it were necessary to make microscope slide preparations of the growing cultures.

Once the microorganisms, such as fungi, have been determined to have grown to a stage which is sufficient to permit their proper identification and diagnosis, which, for fungi, will generally be when the fungi have formed conidia, the user may make a proper identification and diagnosis of the microorganisms by simply placing the slide system apparatus of the invention on the microscope, and viewing the undisturbed, growing microorganisms through the slide system apparatus of the invention. No microscope slide preparation are necessary for such identification and diagnosis.

If the user would like to make a permanent record of the diagnosed fungi (or other microorganisms), the user may, optionally, make a permanent microscope slide of the identified and diagnosed fungi to keep indefinitely in the user's files.

Microscope slides of any type which may be employed to view a sample of microorganisms under a microscope should be labeled with the specimen number and other pertinent details, such as the medium used and the age of the culture, with the use of a permanent marker.

In order to prepare a permanent microscope slide with a sample of the growing fungi 13 (or other microorganisms), one or more drops of lactophenol cotton blue stain, lactol phenol basic fuchsin stain, or any of a variety of Myco-Perm™ stains or other suitable stains or mounting fluids should be placed onto the center area of the microscope slide. The cover sheet 6 should then be gently peeled away from the open end of the compartment 8 in any manner, in any direction, and to any extent, which allows the cover glass to be removed, for example, with sterile forceps. The side of the cover glass which had been in contact with the growing fungi 13 should then be gently placed on top of the drop(s) of stain present on the microscope slide. The stain should be allowed to spread evenly under the cover glass prior to observing the fungi preparation. If Myco-Perm™ stain is employed, the fungi 13 should stain blue. Although a fungal preparation made with Myco-Perm™ stain can be viewed immediately under a microscope, it will take several hours for the microscope slide to completely dry, and to become a permanent slide.

The permanent microscope slide may then also be viewed under a microscope, and the fungi 13 present on the slide may be properly identified (diagnosed) in a manner known by those of skill in the art. This permanent microscope slide may then be maintained in the user's files indefinitely.

In the case in which a permanent microscope slide is not desired by the user, once the growing fungi 13 (or other microorganisms) have matured to the extent necessary to properly identify the fungi 13 (or other microorganisms), and the fungi 13 (or other microorganisms) have been properly identified, the culture may be discarded by autoclaving the entire slide system apparatus 1 in a manner known by those of skill in the art with a commercially-available autoclave for about fifteen minutes to about twenty minutes at about fifteen pounds of pressure, with about fifteen minutes being preferred.

TYPES OF FUNGI

The methods, apparatuses and kits of the present invention may be employed to grow and/or identify with the use of a microscope any type of fungi, such as dimorphic fungi, filamentous fungi, hyalene fungi, dermatopytes, monomorph molds and dermatiaceous fungi. Examples of fungi which may be grown and/or identified in accordance with the methods, apparatus and kits of the invention include *Trichophyton tonsurans, Trichophyton mentagrophytes, Microsporum gypseum, Microsporum nanum, Microsporum canis, Microsporum audouinii, Microsporum vanbreuseghemii, Rhizopus species, Mucor species, Absidia species, Wangiella dermatitidis, Phialophora pedrosei, Philaphora verrucosa, Sporothrix schenckii, Scedosporium apiospermum, Cladosporium carrionil, Aspergillus niger, Aspergillus funigatus, Aspergillus flavus, Penicillum species, Scopulariopsis species, Coccidioides inmitis, Fusarium species, Acremonium species, Epidermophyton floccosum, Blastomyces dermatitidis, Candida albicans, Candida krusei, Streptomyces species,* and *Nocardia species.*

The methods, apparatuses and kits of the present invention may also be used to grow and/or identify other types of microorganisms, such as various types of bacteria, rickettsiae, viruses, yeasts and protozoa. Where a slide system apparatus of the invention 1 contains more than one compartment 3, the same or different types of microorganisms may be grown and/or identified in the separate compartments.

STERILE CONDITIONS

The methods, apparatuses and kits of the present invention should be employed under sterile conditions, and the apparatuses should be sterilized prior to use with, for example, gamma sterilization at a tolerance level of about 1,000 kgy. Cover glasses and forceps may be sterilized by autoclaving, or by soaking them in 70% ethanol and then flaming them. Aseptic technique should be employed throughout the methods, and all work should preferably be performed in a biological safety cabinet.

STABILITY OF APPARATUSES

Slide system apparatuses of the present invention 1, and kits containing these systems, have been found to be stable in their dehydrated form for a period of at lease about one year, with stability of greater than one year being possible depending on the media type. Thus, such slide system apparatuses and kits may be stored for a period of about one year prior to use. Once a slide system apparatus 1 of the invention is hydrated in the manner described hereinabove, the slide system apparatus 1 should be used within a period of about two hours, preferably with in a period of about one-half of an hour, with immediate use being most preferred.

QUALITY CONTROL

To ensure quality control of the slide system apparatuses of the present invention 1, a known fungal or other sample should be tested with each box of slide system apparatuses of the present invention 1. A box of slide system apparatuses of the present invention 1 will generally consist of about ten individual slide system apparatuses 1. The experimental results obtained with the slide system apparatuses of the invention 1 should then be compared with the results of the known fungal or other slide system apparatus in a manner known by those of skill in the art.

b. Advantages of the Apparatuses, Kits and Processes

The following advantages have been observed through the preparation and use of the apparatuses, kits and processes of the present invention:

(1) no microscope slides need ever be prepared in order to view and properly identify microorganisms growing therein (because the slide system apparatuses of the invention may be placed on a microscope, and the microorganisms growing therein may be viewed and identified through these apparatuses;

(2) the growing cultures may be repeatedly viewed and/or diagnosed without being disturbed (because microscope slides need not be prepared in order to perform such viewing and diagnosis);

(3) the slide system apparatuses of the invention are essentially closed systems which virtually eliminate any risk of contamination to the fungi growing therein;

(4) the slide system apparatuses of the invention contain an opening through which air can flow from the outside environment to the growing cultures which is small enough to prevent contaminants from entering a compartment present in the apparatus;

(5) the slide system apparatuses of the invention are inexpensive, and eliminate the need for costly additional equipment, such as petri dishes, microscope slides and laminate flow hoods;

(6) the slide system apparatuses of the invention may be used anywhere that there is a microscope (in a physician's office, in a laboratory, in the jungle, etc.);

(7) the slide system apparatuses of the invention permit a significantly more rapid diagnosis of microorganisms, with significantly fewer steps, than with currently-employed methods for identifying microorganisms;

(8) the slide system apparatuses of the invention may be disposed of easily after use with autoclaving; and (9) the slide system apparatuses and kits of the invention may be stored for a period of about one year.

3. Utility

The methods, slide system apparatuses and kits of the present invention are useful for the culturing and/or identification (diagnosing) of microorganisms, such as fungi, from a sample known to contain, or suspected of containing, some type of microorganism. The microorganisms growing in these slide system apparatuses may be viewed under a microscope through the slide system apparatuses, and may be properly identified, without having to make a microscope slide preparation of the microorganisms and, thus, without having to disturb the growing microorganisms. Such growth and identification of microorganisms may take place anywhere that there is a microscope, for example, in a doctor's office, in a diagnostic laboratory, or even in the jungle.

4. Methods of Preparation

The slide system apparatuses 1 of the present invention may be mass, individually or otherwise produced using readily-available starting materials, equipment and conventional preparation and production procedures, or by modifications thereof, known by those of skill in the art.

For example, commercially-available media may be adsorbed into commercially-available select support matrices 4, sized to a desired size. The solid support matrices 4 may then be heated in an oven heated to 90° C. for two minutes in order to permit the media to dry (to become dehydrated). The unitary member 2 may be unwound from a roll of material. It may then be heated and, while it is in a molten state, have compartments, chambers or wells 3, protrusion, sides and a base injection molded therein. The resulting structure may then be passed through a filler, and the filler may load the solid support matrices 4 which have had dehydrated media 5 applied thereto or therein, and which have been cut to the desired size by methods and equipment known by those of skill in the art, into the compartments 3 formed in the structure 2. Cover sheets 6 containing an appropriate adhesive 7 in the form of a tape with the desired size of cover sheets cut therein may, meanwhile, be unwinding from a second roll of material (Art Tape and Label Corp., Addison, Ill.). This material may then be positioned over the compartments 3 formed in the unitary member 2. This laminate may then be heat or otherwise sealed to the structure containing the compartments 3 in a manner, and with equipment, known by those of skill in the art. The resulting structure may then be die cut into individual slide system apparatuses 1 of the desired size, and containing the desired number of compartments 3, with a steel rule die under pressure.

Alternately, the slide system apparatuses 1 of the invention may be assembled individually by hand with the use of each of the commercially-available components of these apparatuses 1. The assembler would simply place a solid support matrix containing dehydrated media into a compartment 3 of the unitary member 2, and then place a cover sheet 6 over the compartment.

The conditions, equipment and methods for carrying out each of the individual steps in the production of the slide system apparatuses 1 of the present invention are conventional, well-known and capable of wide variation. Other methods known in the art may also be employed to manufacture the slide system apparatuses of the present invention 1. For example, materials and methods other than those described herein may be employed to adhere the cover sheets 6 to the unitary member 2. Those of skill in the art will readily understand that known variations of the conditions and processes of the preparative procedures described herein can be used to prepare the slide system apparatuses 1 of the present invention, and that other methods known in the art can also be used to produce the slide system apparatuses of the present invention 1.

All starting materials and equipment used to prepare the slide system apparatuses 1 and kits of the present invention are commercially available from sources known by those of skill in the art, for example, from Mead Johnson (Division of Bristol-Meyers, Bellevue, Ontario, Canada); Sigma Chemical Co. (St. Louis, Mo.); James River Corp. (Milford, N.J.); Reynolds Metals Company (Richmond, Va.); Dupont (Wilmington, Del.); Morton Chemicals (Chicago, Ill.); KlocknerPentaplast of America, Inc. (Gordonsville, Va.); Uhlmann Packaging Systems, Inc. (Fairfield, N.J.); Aylward Enterprises, Inc. (New Bern, N.C.); Service Industries Midwest, Inc. (Rolling Meadows, Ill.); Art Tape and Label Corp. (Addison, Ill.); and American Filtrona Company (Richmond, Va.).

Although two preferred embodiments of the slide system apparatuses of the present invention have been shown and described herein, those of ordinary skill in the art will recognize numerous modifications and substitutions of that which has been described herein which may be made therein, as by adding, combining, subdividing parts or steps, or by substituting equivalents, while retaining significant advantages of the slide system apparatuses of the present invention, which are defined in the following claims. It is intended, therefore, that all of these modifications and variations be within the scope and spirit of the present invention as described and claimed herein, and that the invention be limited only by the scope of the claims which follow, and that such claims be interpreted as broadly as possible.

While the various aspects of the present invention are described herein with some particularity, those of skill in the art will recognize numerous modifications and variations which remain within the spirit of the invention. These modifications and variations are within the scope of the invention as described and claimed herein.

While the present invention has been described herein with some specificity, and with reference to certain preferred embodiments thereof, those of ordinary skill in the art will recognize numerous variations, modifications, and substitutions of that which has been described which can be made, and which are within the scope and spirit of the invention. Likewise, the specific effect observed may vary according to, and depending upon, the particular type of fungi, or other microorganisms being grown, the particular needs of the mycologist or other user, or upon whether special conditions exist. Such expected variations and/or differences in the results are contemplated in accordance with the objects and practices of the present invention. It is intended therefore that all of these modifications and variations be within the scope of the present invention as described and claimed herein, and that the invention be limited only by the scope of the claims which follow, and that such claims be interpreted as broadly as is reasonable.

What is claimed is:

1. A slide system apparatus for the growth and/or identification of microorganisms comprising:
   (1) a unitary member containing one or more compartments in which microorganisms may grow, and containing one or more openings through which air may flow from the outside environment into each of said compartments;
   (2) one or more porous support matrices present in each of the compartments present in the unitary member;
   (3) dehydrated media present within, or on one or more surfaces of, each of the solid support matrices; and
   (4) a cover sheet lying over the open end of each compartment and secured to the upper surfaces of the unitary member which surround the open end of each compartment, and having a pull tab.

2. The slide system apparatus of claim 1 wherein the slide system apparatus is for the growth and/or identification of fungi.

3. The slide system apparatus of claim 1 wherein the slide system apparatus contains more than one compartment.

4. The slide system apparatus of claim 2 wherein the slide system apparatus contains more than one compartment.

5. The slide system apparatus of claim 1 wherein the cover sheet may be repeatedly removed from, and readhered to, the slide system apparatus.

6. The slide system apparatus of claim 2 wherein the cover sheet may be repeatedly removed from, and readhered to, the slide system apparatus.

7. The slide system apparatus of claim 1 which further comprises a cover glass.

8. The slide system apparatus of claim 2 which further comprises a cover glass.

9. The slide system apparatus of claim 1 wherein each of the openings has a shape formed by a series of curves or right angles.

10. The slide system apparatus of claim 2 wherein each of the openings has a shape formed by a series of curves or right angles.

11. The slide system apparatus of claim 1 which further comprises one or more protrusions present in each of said compartments.

12. The slide system apparatus of claim 2 which further comprises one or more protrusions present in each of said compartments.

13. The slide system apparatus of claim 1 wherein the slide system apparatus may be stored for about one year prior to use.

14. The slide system apparatus of claim 2 wherein the slide system apparatus may be stored for about one year prior to use.

15. The slide system apparatus of claim 3 wherein the slide system apparatus is rectangular in shape and contains two square compartments.

16. The slide system apparatus of claim 4 wherein the slide system apparatus is rectangular in shape and contains two square compartments.

17. The slide system apparatus of claim 15 wherein the slide system apparatus is made of polystyrene, is about 25.4 mm in width, about 76.5 mm in length and about 8 mm in height, the compartments are about 17 mm by about 17 mm in width and about 8 mm in height, and the porous support matrices are made of cellulose acetate, are in the shape of a doughnut, and are about 11.5 mm wide and have a hole which is about 6 mm wide.

18. The slide system apparatus of claim 16 wherein the slide system apparatus is made of polystyrene, is about 25.4 mm in width, about 76.5 mm in length and about 8 mm in height, the compartments are about 17 mm by about 17 mm in width and about 8 mm in height, and the porous support matrices are made of cellulose acetate, are in the shape of a doughnut, and are about 11.5 mm wide and have a hole which is about 6 mm wide.

19. The slide system apparatus of claim 17 wherein the dehydrated media is dextrose broth.

20. The slide system apparatus of claim 18 wherein the dehydrated media is dextrose broth.

21. A kit for the growth and/or identification of microorganisms comprising:

(1) a slide system apparatus comprising:
  (a) a unitary member containing one or more compartments in which microorganisms may grow, and containing one or more openings through which air may flow from the outside environment into each of said compartments;
  (b) one or more porous support matrices present in each of the compartments present in the unitary member;
  (c) dehydrated media present within, or on one or more surfaces of, each of the solid support matrices;
  (d) a cover sheet 6 lying over the open end of each compartment and secured to the upper surfaces of the unitary member which surround the open end of each compartment, and having a pull tab; and (2) one or more:
  (a) hydrating liquids;
  (b) cover glasses;
  (c) tools for inoculating the solid support matrices with a sample containing microorganisms;
  (d) tools for grasping other items present within the kit;
  (e) microscope slides;
  (f) reagents for staining samples of microorganisms; and/or
  (g) reagents for making a permanent microscope slide stain preparations.

\* \* \* \* \*